(12) United States Patent
Againe Csongor et al.

(10) Patent No.: US 7,705,003 B2
(45) Date of Patent: Apr. 27, 2010

(54) CYCLOHEXYLAMIDES AS DOPAMINE D3, D2 AND 5-HT$_{1A}$ ANTAGONISTS

(75) Inventors: Eva Againe Csongor, Budapest (HU); Janos Galambos, Budapest (HU); Istvan Gyertyan, Budapest (HU); Bela Kiss, Budapest (HU); Katalin Saghy, Budapest (HU); Eva Schmidt, Budapest (HU); Gyoergy Domany, Budapest (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 219 days.

(21) Appl. No.: 11/814,874

(22) PCT Filed: Feb. 2, 2006

(86) PCT No.: PCT/HU2006/000012

§ 371 (c)(1),
(2), (4) Date: Jul. 26, 2007

(87) PCT Pub. No.: WO2006/082456

PCT Pub. Date: Aug. 10, 2006

(65) Prior Publication Data

US 2008/0103140 A1    May 1, 2008

(30) Foreign Application Priority Data

Feb. 3, 2005   (HU) .................................. 0500170

(51) Int. Cl.
*A61K 31/4965* (2006.01)
*C07D 241/04* (2006.01)
*C07D 295/00* (2006.01)

(52) U.S. Cl. .................. 514/255.03; 544/400
(58) Field of Classification Search ............ 514/255.03; 544/400, 402
See application file for complete search history.

(56) References Cited

U.S. PATENT DOCUMENTS 6,531,236 B1 * 3/2003 Hatoh et al. .................. 429/34

OTHER PUBLICATIONS

Andersson, et al., CNS Involvement in Overactive Bladder, Drugs, 63 (23), 2505-2611 (2003).*

* cited by examiner

*Primary Examiner*—James O Wilson
*Assistant Examiner*—Erich A Leeser
(74) *Attorney, Agent, or Firm*—Darby & Darby, P.C.

(57) ABSTRACT

The present invention relates to new dopamine D$_3$ and D$_2$ and serotonin 5-HT$_{1A}$ receptor subtype preferring ligands of formula (I); wherein A represents alkyl, alkenyl, aryl, heteroaryl, cycloalkyl or a group of formula —NR$_1$R$_2$, wherein R$_1$ and R$_2$ represent independently a substituent selected from hydrogen, alkyl, alkenyl, aryl, heteroaryl or cycloalkyl or R$_1$ and R$_2$ form with the adjacent nitrogen atom and optionally with further heteroatom(s) a heterocyclic ring; m is an integer of 0 to 1; n is an integer of 1 to 2, and/or geometric isomers and/or stereoisomers and/or diastereomers and/or salts and/or hydrates and/or solvates thereof, to the processes for producing the same, to pharmacological compositions containing the same and to their use in therapy and/or prevention of a condition which requires modulation of dopamine and/or 5-HT$_{1A}$ receptors.

(I)

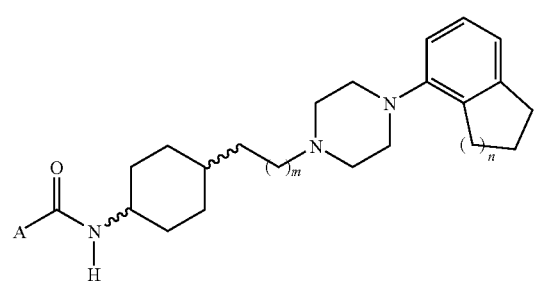

12 Claims, No Drawings

CYCLOHEXYLAMIDES AS DOPAMINE D3, D2 AND 5-HT$_{1A}$ ANTAGONISTS

This application is a national phase of PCT Application No. PCT/HU2006/000012, filed Feb. 2, 2006, which was published in English as International Publication No. WO 2006/082456, and claims the benefit of Hungarian Patent Application No. P 0500170, filed Feb. 3, 2005.

FIELD OF THE INVENTION

The present invention relates to new dopamine D$_3$ and D$_2$ and serotonin 5-HT$_{1A}$ receptor subtype preferring ligands of formula (I) and/or geometric isomers and/or stereoisomers and/or diastereomers and/or salts and/or hydrates and/or solvates thereof, to the processes for producing the same, to pharmacological compositions containing the same and to their use in therapy and/or prevention of a condition which requires modulation of dopamine and/or 5-HT$_{1A}$ receptors.

DESCRIPTION OF THE PRIOR ART

Cyclohexane derivatives being useful in the therapy for the treatment of pain are described in patent application WO 99/67206.

Compounds containing both tetraline and piperazine rings, are described in JP 1998152470. The compounds possess potent blocking activities against D$_4$ receptors and high affinities for serotonin-2 (5-HT$_2$), muscarinic (M$_1$) and adrenergic alpha 1 and alpha 2 receptors.

Such compounds, however, which contain cyclohexane, indane or tetraline and piperazine ring together in one compound, are not mentioned in any publication.

Besides, the compounds mentioned in the above publications are not declared or even not suggested having activity on the dopamine D$_3$ and/or D$_2$ and/or serotonin 5-HT$_{1A}$ receptors.

SUMMARY OF THE INVENTION

Surprisingly it was found that in contrast to the known above mentioned structurally analogous compounds the new derivatives of formula (I) of the present invention have high or very high affinity to dopamine D$_3$ receptors and moderate to high affinity to dopamine D$_2$ receptors always in such a combination that the D$_3$ affinity is 5 to 150 fold higher than the D$_2$ affinity. Moreover, the compounds have also high affinity to serotonin 5-HT$_{1A}$ receptors but their affinity to these receptors is 3-20 fold less than to dopamine D$_3$ receptors. The order of receptor binding potency of the compounds of formula (I) is typically the following: D$_3$>5-HT$_{1A}$>D$_2$. Their affinity to alpha-1 adrenoceptors is mild assuring high (i.e. 50-800 fold) D$_3$ selectivity.

The threefold (i.e. D$_3$, D$_2$ and 5-HT$_{1A}$) receptor functional antagonism coupled in the above mentioned particular proportion is especially important as it allows the simultaneous manifestation of the beneficial effects of modulation of all the three (D$_3$, D$_2$ and 5-HT$_{1A}$) receptors, however, without the appearance of the known disadvantages of each individual receptor action.

This type of new molecules belonging to the structure of formula (I) will be referred further on in this application as "D$_3$/5-HT$_{1A}$/D$_2$ ligands".

The invention relates to new piperazine derivatives of formula (I):

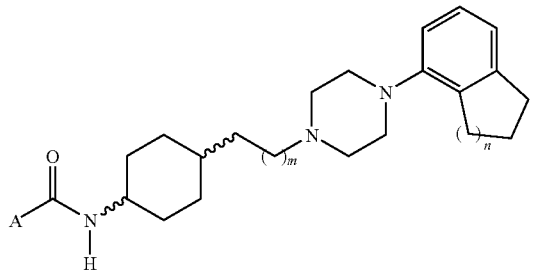

wherein
A represents alkyl, alkenyl, aryl, heteroaryl, cycloalkyl or a group of formula —NR$_1$R$_2$, wherein
R$_1$ and R$_2$ represent independently a substituent selected from hydrogen, alkyl, alkenyl, aryl, heteroaryl or cycloalkyl or R$_1$ and
R$_2$ form with the adjacent nitrogen atom and optionally with further heteroatom(s) a heterocyclic ring;
m is an integer of 0 to 1;
n is an integer of 1 to 2, and/or geometric isomers and/or stereoisomers and/or diastereomers and/or salts and/or hydrates and/or solvates thereof, to the processes for producing the same, to pharmacological compositions containing the same and to their use in therapy and/or prevention of pathological conditions which require the modulation of dopamine and/or serotonin receptors such as psychoses (e.g. schizophrenia, schizo-affective disorders, etc.), drug (e.g. alcohol, cocaine and nicotine, opioids, etc.) abuse, cognitive impairment accompanying schizophrenia, mild-to-moderate cognitive deficits, dementia, psychotic states associated with dementia, eating disorders (e.g. bulimia nervosa, etc.), attention deficit disorders, hyperactivity disorders in children, psychotic depression, mania, bipolar disorder, paranoid and delusional disorders, dyskinetic disorders (e.g. Parkinson's disease, neuroleptic induced parkinsonism, tardive dyskinesias), depression and depressive states, anxiety disorders, sexual dysfunction, sleep disorders, emesis, aggression, autism.

DETAILED DESCRIPTION OF THE INVENTION

The invention relates to new piperazine derivatives of formula (I):

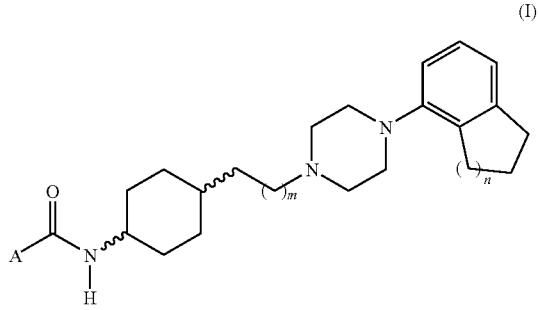

wherein
A represents alkyl, alkenyl, aryl, heteroaryl, cycloalkyl or a group of formula —NR$_1$R$_2$, wherein
R$_1$ and R$_2$ represent independently a substituent selected from hydrogen, alkyl, alkenyl, aryl, heteroaryl or cycloalkyl or R$_1$ and R$_2$ form with the adjacent nitrogen atom and optionally with further heteroatom(s) a heterocyclic ring;
m is an integer of 0 to 1;
n is an integer of 1 to 2, and/or geometric isomers and/or stereoisomers and/or diastereomers and/or salts and/or hydrates and/or solvates thereof.

When A or R$_1$ and/or R$_2$ represent alkyl, the alkyl moiety may be selected from an optionally substituted straight or branched chain containing 1 to 6 carbon atoms.

When A or R$_1$ and/or R$_2$ represent alkenyl, the alkenyl moiety may contain 2 to 7 carbon atoms and 1 to 3 double bonds.

When A or R$_1$ and/or R$_2$ represent aryl, the aryl moiety may be selected from an optionally substituted mono- or bicyclic aryl, such as phenyl, naphthyl group.

When A or R$_1$ and/or R$_2$ represent cycloalkyl, the cycloalkyl moiety may be selected from an optionally substituted mono-, bi- or tricyclic cycloalkyl group, such as cyclohexyl or adamantyl.

When A or R$_1$ and/or R$_2$ represent heteroaryl, the heteroaryl may be an optionally substituted monocyclic, bicyclic or tricyclic aromatic heterocyclic group containing 1 to 6 heteroatoms selected from O, N or S.

When R$_1$ and R$_2$ form with the adjacent nitrogen atom a heterocyclic ring it may be saturated or unsaturated, optionally substituted monocyclic or bicyclic ring, which may contain further heteroatoms selected from O, N, or S.

The invention relates also to the salts of compounds of formula (I) formed with acids.

Both organic and inorganic acids can be used for the formation of acid addition salts. Suitable inorganic acids can be for example hydrochloric acid, sulfuric acid, nitric acid and phosphoric acid. Representatives of monovalent organic acids can be for example formic acid, acetic acid, propionic acid, and different butyric acids, valeric acids and capric acids. Representatives of bivalent organic acids can be for example oxalic acid, malonic acid, maleic acid, fumaric acid and succinic acid. Other organic acids can also be used, such as hydroxy acids for example citric acid, tartaric acid, or aromatic carboxylic acids for example benzoic acid or salicylic acid, as well as aliphatic and aromatic sulfonic acids for example methanesulfonic acid, naphtalenesulfonic acid and p-toluenesulfonic acid. Especially valuable group of the acid addition salts is in which the acid component itself is physiologically acceptable and does not have therapeutical effect in the applied dose or it does not have unfavourable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and isolation of the desired compounds.

Solvates and/or hydrates of compounds of formula (I) are also included within the scope of the invention.

The compounds of formula (I) exist in the form of cis and trans isomers with respect to the configuration of the cyclohexane ring. These and their mixtures are likewise within the scope of the present invention. The compounds of the invention are preferably in trans configuration.

Certain compounds of formula (I) when the compound contains C$_{2-7}$ alkenyl group can exist in the form of cis- and/or trans-isomers. These are likewise within the scope of the present invention including all such isomers and the mixtures thereof.

Certain compounds of formula (I) can exist as stereoisomers and diastereomers, too. These and the mixtures thereof are likewise within the scope of the present invention.

As the invention relates also to the salts of compounds of formula (I) formed with acids, especially the salts formed with pharmaceutically acceptable acids, the meaning of compound of formula (I) is either the free base or the salt even if it is not referred separately.

Preferred compounds of the invention are those compounds of formula (I):

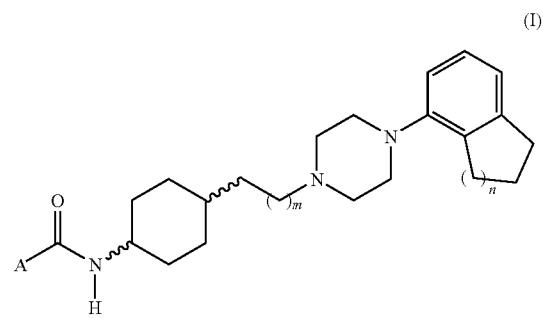

wherein
A represents alkyl, or
a group of formula —NR$_1$R$_2$, wherein
R$_1$ and R$_2$ represent independently a substituent selected from hydrogen or alkyl, or R$_1$ and R$_2$ form with the adjacent nitrogen atom and optionally with further heteroatom(s) selected from O, N, or S a monocyclic saturated heterocyclic ring;
m is an integer of 0 to 1;
n is an integer of 1 to 2, and/or geometric isomers and/or stereoisomers and/or diastereomers and/or salts and/or hydrates and/or solvates thereof.

Particularly preferred compounds of the invention are those compounds of formula (I):

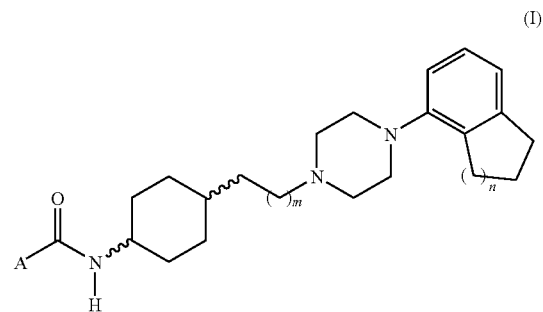

wherein

A represents $C_{1-4}$ alkyl, or a group of formula $—NR_1R_2$, wherein $R_1$ and $R_2$ represent independently a substituent selected from hydrogen or $C_{1-4}$ alkyl, or $R_1$ and $R_2$ form with the adjacent nitrogen atom and an oxygen atom a morpholine ring;

m is an integer of 0 to 1;

n is an integer of 1 to 2, and/or geometric isomers and/or stereoisomers and/or diastereomers and/or salts and/or hydrates and/or solvates thereof.

The invention also relates to the pharmaceutical compositions containing the compounds of formula (I) as active ingredient.

Further subject of the present invention is the pharmaceutical manufacture of medicaments containing compounds of formula (I), as well as the process of treatments and/or prevention with these compounds, which means administering to a mammal to be treated—including human—effective amount/amounts of compounds of formula (I) of the present invention as such or as medicament.

The present invention also provides a process (Method A) for preparing compounds of formula (I):

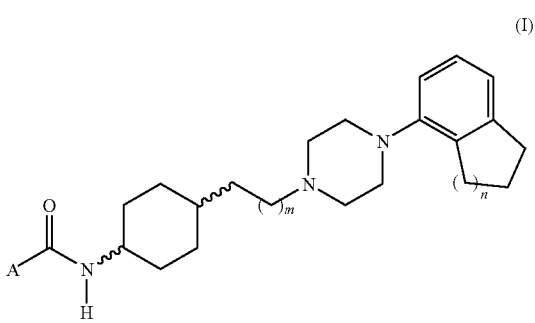

(I)

wherein

A represents alkyl, alkenyl, aryl, heteroaryl, cycloalkyl or a group of formula $—NR_1R_2$, wherein $R_1$ and $R_2$ represent independently a substituent selected from hydrogen, alkyl, alkenyl, aryl, heteroaryl or cycloalkyl or $R_1$ and $R_2$ form with the adjacent nitrogen atom and optionally with further heteroatom(s) a heterocyclic ring;

m is an integer of 0 to 1;

n is an integer of 1 to 2, by reacting an acid- or carbamoylchloride of formula (II):

(II)

wherein A is as described above for the formula (I);

with an amine of formula (III):

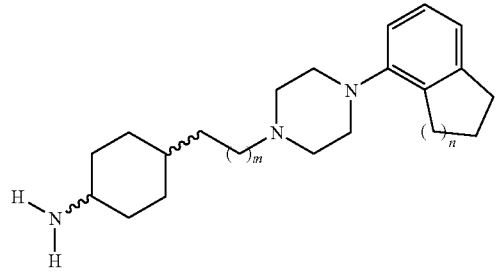

(III)

wherein the meaning of m and n is as described above for the formula (I), or derivatives thereof.

The reaction may be carried out by known methods, preferably by suspending or dissolving the appropriate amine of formula (III) or a salt thereof in a suitable solvent (e.g. tetrahydrofurane, dimethylformamide or chlorinated hydrocarbons or hydrocarbons) and adding the appropriate acid- or carbamoylchloride of formula (II) to this suspension or solution, in the presence of a base (e.g. triethylamine). The reaction can be carried out advantageously between −10° C. and 60° C. The reactions are followed by thin layer chromatography. The necessary reaction time is about 6-60 h. The workup of the reaction mixture can be carried out by different known methods. The products can be purified, e.g. by crystallization or by column chromatography.

Another process (Method B) of the present invention for preparing the compounds of formula (I):

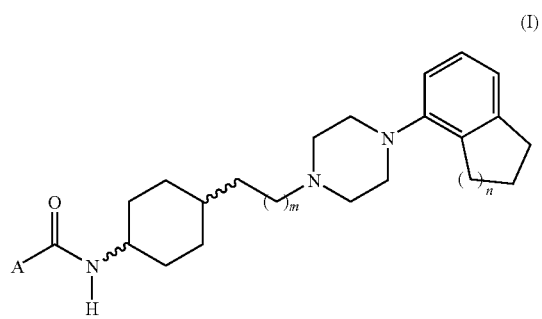

(I)

wherein

A represents a group of formula $—NR_1R_2$, wherein $R_2$ represents hydrogen, and $R_1$ represents a substituent selected from hydrogen, alkyl, alkenyl, aryl, heteroaryl or cycloalkyl;

m is an integer of 0 to 1;

n is an integer of 0 to 2, is reacting the isocyanate of formula (IV):

$$R_1—N=C=O \quad (IV)$$

wherein the meaning of $R_1$ is as described above for the formula (I), with an amine of formula (III):

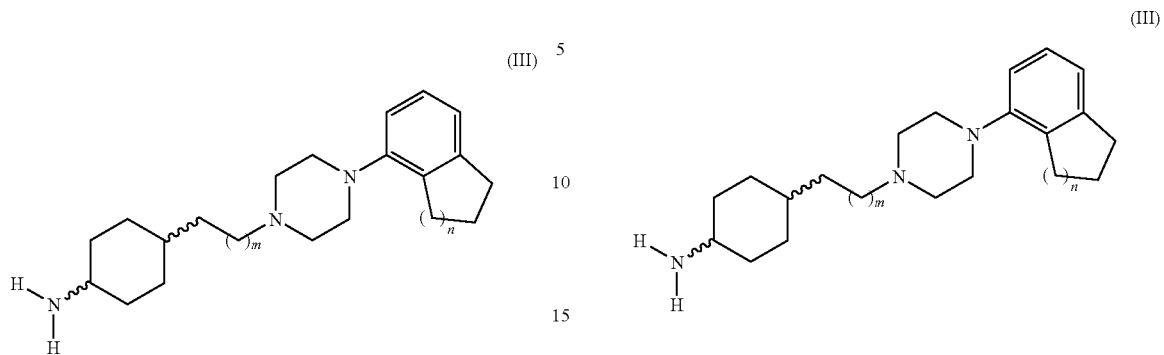

wherein the meaning of m and n is as described above for the formula (I), or derivatives thereof.

The reaction may be carried out by known methods, preferably by suspending or dissolving the appropriate amine of formula (III) or a salt thereof in a suitable solvent (e.g. tetrahydrofurane, dimethylformamide or chlorinated hydrocarbons or hydrocarbons) and adding the appropriate isocyanates of formula (IV) to this suspension or solution, if necessary, in the presence of a base (e.g. triethylamine). The reaction can be carried out advantageously between 5° C. and 50° C. The reactions are followed by thin layer chromatography. The necessary reaction time is about 6-10 h. The work-up of the reaction mixture can be carried out by different known methods. The products can be purified, e.g. by crystallization or by column chromatography.

Another process (Method C) of the present invention for preparing compounds of formula (I):

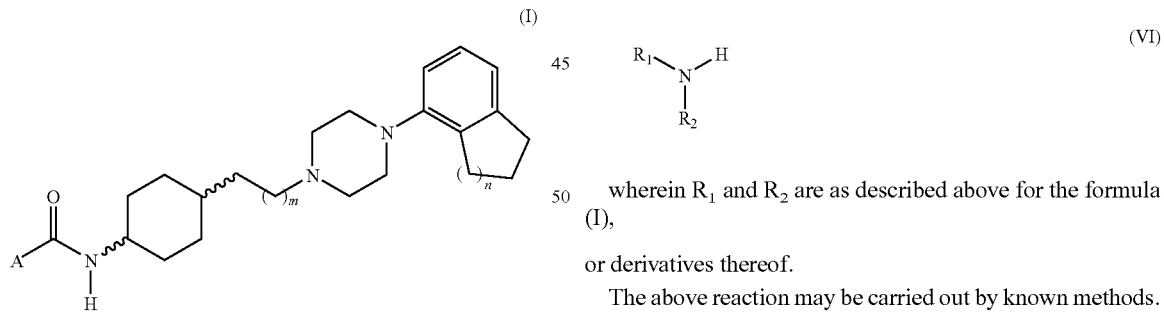

wherein

A represents a group of formula —NR$_1$R$_2$, wherein

R$_1$ and R$_2$ represent independently a substituent selected from hydrogen, alkyl, alkenyl, aryl, heteroaryl or cycloalkyl or R$_1$ and R$_2$ form with the adjacent nitrogen atom and optionally with further heteroatom(s) a heterocyclic ring;

m is an integer of 0 to 1;

n is an integer of 1 to 2, is reacting an amine of formula (III):

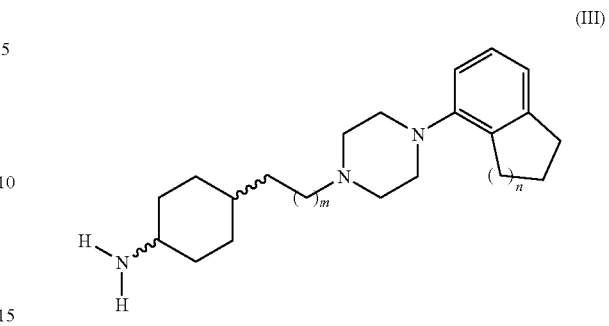

wherein the meaning of m and n is as described above for the formula (I), or derivatives thereof, with a carbonic acid derivative to obtain an isocyanate derivative of formula (V):

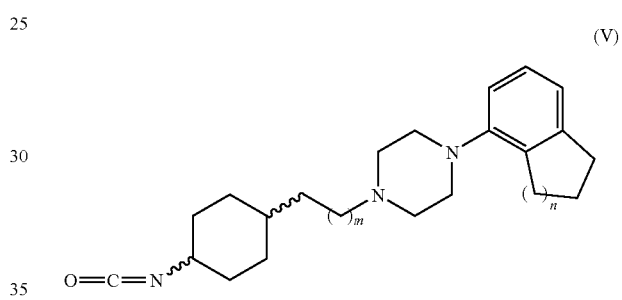

wherein the meaning of m and n is as described above for the formula (I), and reacting in situ the new isocyanate derivative of formula (V) with an amine of formula (VI):

$$R_1\text{—}NH\text{—}R_2 \quad (VI)$$

wherein R$_1$ and R$_2$ are as described above for the formula (I), or derivatives thereof.

The above reaction may be carried out by known methods. Preferably the transformation an amine of formula (III) to isocyanate derivative of formula (V) may be carried out in an aprotic solvent (e.g. tetrahydrofurane, chlorinated hydrocarbons) by the use of an appropriate carbonic acid derivative (e.g. phosgene, diphosgene, triphosgene) in the presence of a base (e.g. triethylamine), advantageously between −5° C. and room temperature. To the thus obtained solution or suspension an appropriate amine of formula (VI) is added in the form of base or salt formed with organic or inorganic acid. The necessary reaction time is between 2-24 hours. The work-up of the reaction mixture can be carried out by different known methods. The products can be purified, e.g. by crystallization or by column chromatography.

The acid- or carbamoylchlorides of formula (II) and isocyanates of formula (IV) and the amines of formula (VI), wherein $R_1$ and $R_2$ are as defined above, are either commercially available or can be synthesized by different known methods.

The amines of formula (III) and the isocyanates of formula (V) wherein m=0 or 1 and n=1 or 2 are new compounds and are also included within the scope of the present invention.

The new amines of formula (III) are synthesized by known methods, e.g. reacting an aldehyde of formula (VII):

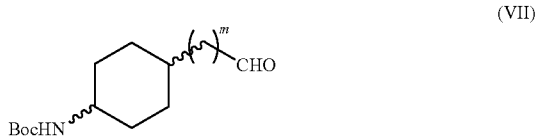

(VII)

wherein the meaning of m is as described above for the formula (I) and Boc is tert-butoxycarbonyl group,
with a piperazine of formula (VIII):

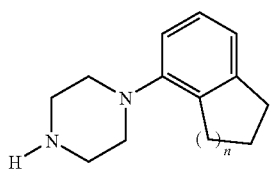

(VIII)

wherein the meaning of n is as described above for the formula (I), under the circumstances of reductive amination, then removing the protecting group.

The reaction may be carried out in an inert solvent (e.g. chlorinated hydrocarbons, alkanols or ethers) in the presence of a reductive agent, for example, sodium borohydride, sodium cyanoborohydride or sodium triacetoxyborohydride. The reaction temperature is usually between 0° C. and room temperature. The necessary reaction time is about 2-24 h. Deprotection may be carried out using trifluoroacetic acid or hydrochloric acid in a suitable solvent.

Compounds of formula (VII) and (VIII) are known (e.g. Bioorg. Med. Chem. Lett. 2001: 11(16) 2177-80; J. Med. Chem. 2000: 43(9) 1878-85; WO 2004/99150; Collection of Czech. Chem. Comm. 1975: 40(5) 1612-22).

The obtained compounds of formula (I) can be transformed into the salts thereof with acids and/or liberated the compounds of formula (I) from the obtained acid addition salts by treatment with a base, and/or the cis- and/or trans-isomers and/or the stereoisomers and/or diastereomers can be separated and/or can be transformed into hydrates and/or solvates thereof.

The separation of cis- and trans isomers either of compounds of formula (I) or of formula (III) or the protected derivatives of the latter, or of formula (V) is carried out by conventional methods, e.g. by chromatography and/or crystallization, or the cis and trans isomers of formula (I) can be prepared from the pure cis or trans precursor.

The compounds of formula (I) of the present invention, in contrast to known psychotropic drugs, have been found to exhibit very high affinity for dopamine $D_3$ receptors, high affinity to serotonin 5-$HT_{1A}$ receptors and moderate activity toward $D_2$ receptors and less affinity to adrenergic alpha-1 receptors. The compounds are expected to be useful in the treatment of disease states and/or prevention the same in which dopamine $D_3$ and/or $D_2$ and/or serotonin 5-$HT_{1A}$ receptors are involved in the disease pathology and thus their modulation is required.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions (Sokoloff, P. et al.: Nature 1990, 347:146; Schwartz, J. C. et al.: Clin. Neuropharmacol. 1993, 16:295; Levant, B.: Pharmacol. Rev. 1997, 49:231), addiction (Pilla, C. et al.: Nature 1999, 400, 371), Parkinson's disease (Levant, B. et al.: CNS Drugs 1999, 12:391, Joyce, J. N.: Pharmacol. Therap. 2001, 90:231), anxiety (Rogoz et al., Pol. J. Pharmacol. 2000, 52:459) or pain (Levant, B. et al.: Neurosci. Lett. 2001, 303:9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation, cognitive disturbances and endocrine alterations. These side effects seriously restrict the therapeutic utilization of $D_2$ antagonist compounds. (Wong, A. H. C. et al.: Neurosci. Biobehav. Rev. 2003, 27:269).

It was found in animal experiments that partial agonism at 5-$HT_{1A}$ receptors enhances antipsychotic actions of dopamine antagonism (Evenden, J. L.: Psychopharmacol. 1992, 109:134.) and may inhibit appearance of catalepsy (predictor of extrapyramidal side effects) the consequence of striatal dopamine $D_2$ receptor blockade (Lucas, G. et al.: Psychopharmacol. 1997, 131:57., Prinssen, E. P. et al.: Eur. J. Pharmacol. 2002, 453:217., Haleem, D. J. et al.: Progr. Neuro-Psychopharmacol. 2004, 28:1323.) It has also been demonstrated that 5-$HT_{1A}$ agonism contributes to increase of prefrontal dopamine release an effect which may be potentially beneficial in negative symptoms and cognitive deficits in schizophrenia (Li, X.-M. et al.: Psychopharmacol. 1998, 136:153., Millan, M. J.: J. Pharmacol. Exp. Ther. 2000, 295: 853; Ichikawa, J. et al. J. Pharmacol. Exp. Ther. 1999, 291: 1227).

Depression and anxiety are frequently co-morbid diseases of schizophrenia (Stahl, S. M.: 2002, Essential Psychopharmacology of Antipsychotics and Mood Stabilizers. Cambridge University Press). 5-$HT_{1A}$ receptors are potential targets in the treatment of anxiety (Barret, J. E. et al.: Psychopharmacol. 1993, 112:1; DeVry, J. Psychopharmacol. 1995, 121:1). Indeed, a partial agonist of 5-$HT_{1A}$ receptors has already been introduced for the treatment of anxiety (Fulton, B. et al.: CNS Drugs 1997, 7:68.) and some others are in clinical testing. Animal experiments also indicate that 5-$HT_{1A}$ agonists may be useful in the treatment of depression (DeVry, J. Psychopharmacol. 1995, 121:1, Koek, W. et al.: J. Pharmacol. Exp. Ther. 1998, 287:266). It is thought, that 5-$HT_{1A}$ agonist properties of some known antipsychotics (Newman-Tancredi, A. et al.: Eur. J. Pharmacol. 1998, 355: 245, Saller, C. F. et al: Psychopharmacol. 1993, 112:285, Jordan, S. et al.: Eur. J. Pharmacol. 2002, 441:137) greatly contributes to their beneficial actions in the treatment of bipolar depression or depressive syndrome of schizophrenia.

The present invention provides novel compounds of formula (I) and/or geometric isomers and/or stereoisomers and/or diastereomers and/or salts and/or hydrates and/or solvates thereof which have very high affinity to dopamine $D_3$ receptors (IC-50 values are less than 2 nM) and—simultaneously—have high affinity to 5-$HT_{1A}$ receptors (IC-50: 1-20 nM) and moderate affinity to $D_2$ receptors (IC-50 values between 10 and 40 nM) always in such combination that the $D_3$ affinity is 5 to 150 higher than the $D_2$ and 3-20 fold higher than the 5-$HT_{1A}$ affinity. The order of receptor binding potency of the compounds of formula (I) is typically the following: $D_3$>5-$HT_{1A}$>$D_2$.

In a further aspect of the present invention it provides a method of treating conditions which require preferential modulation of dopamine $D_3$, and/or $D_2$ and/or serotonin 5-$HT_{1A}$ receptors, for example psychoses (e.g. schizophrenia, schizo-affective disorders), cognitive impairment accompanying schizophrenia, mild-to-moderate cognitive deficits, dementia, psychotic states associated with dementia, psychotic depression, mania, bipolar disorder, paranoid and delusional disorders, dyskinetic disorders such as Parkinson's disease, neuroleptic induced parkinsonism, tardive dyskinesia, eating disorders (e.g. bulimia nervosa), attention deficit disorders, hyperactivity disorders in children, depression and depressive states, anxiety disorders, sexual dysfunction, sleep disorders, emesis, aggression, autism and drug abuse, which comprises administering to a subject in need thereof an effective amount of a compound of formula (I) and/or geometric isomers and/or stereoisomers and/or diastereomers and/or salts and/or hydrates and/or solvates thereof.

The invention also provides the use of a compound of formula (I) and/or geometric isomers and/or stereoisomers and/or diastereomers and/or salts and/or hydrates and/or solvates thereof in the manufacture of a medicament for the treatment of conditions which require modulation of dopamine and/or serotonin receptors especially that of dopamine D3 and/or D2 and/or serotonin 5-HT1A receptors.

A preferred use for $D_3$/5-$HT_{1A}$/$D_2$ ligands according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, paranoid and delusional disorders, dyskinetic disorders such as Parkinson's disease, neuroleptic induced parkinsonism, depression and depressive states, anxiety disorders, drug abuse (e.g. cocaine abuse).

The particular combination of the three receptor-actions described above allows the simultaneous manifestation of the beneficial actions of both the $D_3$ antagonism and 5-$HT_{1A}$ functional antagonism (e.g. cognitive enhancer effect, inhibition of extrapyramidal motor symptoms, inhibitory action on drug abuse, anxiolysis and antidepressant action) and that of the $D_2$ antagonism (e.g. antipsychotic effect). Furthermore, the same combination surprisingly results in cancelling out the disadvantageous features of $D_2$ antagonism (e.g. extrapyramidal symptoms, psychomotor sedation, cognitive disturbances).

For use in medicine, the compounds of formula (I) of the present invention and/or geometric isomers and/or stereoisomers and/or diastereomers and/or physiologically acceptable salts and/or hydrates and/or solvates thereof are usually administered as a standard pharmaceutical composition. The present invention therefore provides in a further aspect pharmaceutical compositions comprising a new compound of formula (I) and/or geometric isomers and/or stereoisomers and/or diastereomers and/or physiologically acceptable salts and/or hydrates and/or solvates thereof and physiologically acceptable carriers.

The compounds of formula (I) of the present invention and/or geometric isomers and/or stereoisomers and/or diastereomers and/or physiologically acceptable salts and/or hydrates and/or solvates thereof may be administered by any convenient method, for example by oral, parental, buccal, sublingual, nasal, rectal or transdermal administration and the pharmaceutical compositions adapted accordingly.

The compounds of formula (I) of the present invention and/or geometric isomers and/or stereoisomers and/or diastereomers and/or physiologically acceptable salts and/or hydrates and/or solvates thereof which are active when given orally can be formulated as liquids or solids, for example syrups, suspensions or emulsions, tablets, capsules and lozenges.

A liquid formulation of the compounds of formula (I) of the present invention and/or geometric isomers and/or stereoisomers and/or diastereomers and/or physiologically acceptable salts and/or hydrates and/or solvates thereof generally consists of a suspension or solution of the compound of formula (I) and/or geometric isomers and/or stereoisomers and/or diastereomers and/or salts and/or hydrates and/or solvates thereof in a suitable liquid carrier(s) for example an aqueous solvent, such as water, ethanol or glycerine, or a non-aqueous solvent, such as polyethylene glycol or an oil. The formulation may also contain a suspending agent, preservative, flavouring or colouring agent.

A composition in the solid form of a tablet can be prepared using any suitable pharmaceutical carrier(s) routinely used for preparing solid formulations. Examples of such carriers include magnesium stearate, starch, lactose, sucrose, cellulose etc.

A composition in the solid form of a capsule can be prepared using routine encapsulation procedures. For example, pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Typical parenteral compositions consist of a solution or suspension of the compound of formula (I) of the present invention and/or geometric isomers and/or stereoisomers and/or diastereomers and/or physiologically acceptable salts and/or hydrates and/or solvates thereof in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions of the present invention for nasal administration containing a compound of formula (I) and/or geometric isomers and/or stereoisomers and/or diastereomers and/or physiologically acceptable salts and/or hydrates and/or solvates thereof may conveniently be formulated as aerosols, drops, gels and powders. Aerosol formulations of the present invention typically comprise a solution or fine suspension of the compound of formula (I) and/or geometric isomers and/or stereoisomers and/or diastereomers and/or physiologically acceptable salts and/or hydrates and/or solvates thereof in a physiologically acceptable aqueous or non-aqueous solvent and are usually presented in a single or multidose quantities in sterile form is a sealed container, which can take the form of a cartridge or refill for use with an atomising device. Alternatively, the sealed container may be a unitary dispensing device, such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas, such as compressed air or an organic propellant, such as a fluorochlorohydrocarbon. The aerosol dosages form can also take the form of a pump-atomiser. Compositions of the present invention containing a compound of formula (I) and/or geometric isomers and/or stereoisomers and/or diastereomers and/or physiologically acceptable salts and/or hydrates and/or solvates thereof suitable for buccal or sublingual administration include tablets, lozenges and pastilles, wherein the active ingredient is formulated with a carrier, such as sugar and acacia, tragacanth, or gelatine and glycerine etc.

Compositions of the present invention containing a compound of formula (I) and/or geometric isomers and/or stereoisomers and/or diastereomers and/or physiologically acceptable salts and/or hydrates and/or solvates thereof for rectal administration are conveniently in the form of suppositories containing a conventional suppository base, such as cocoa butter.

Compositions of the present invention containing a compound of formula (I) and/or geometric isomers and/or stereoisomers and/or diastereomers and/or physiologically acceptable salts and/or hydrates and/or solvates thereof for transdermal administration include ointments, gels and patches.

The compositions of the present invention containing a compound of formula (I) and/or geometric isomers and/or stereoisomers and/or diastereomers and/or physiologically acceptable salts and/or hydrates and/or solvates thereof are preferably in the unit dose form, such as tablet, capsule or ampoule.

Each dosage unit of the present invention for oral administration contains preferably from 1 to 250 mg of a compound of formula (I) and/or geometric isomers and/or stereoisomers and/or diastereomers and/or physiologically acceptable salts and/or hydrates and/or solvates thereof calculated as a free base.

Each dosage unit of the present invention for parenteral administration contains preferably from 0.1 to 2 mg of a compound of formula (I) and/or geometric isomers and/or stereoisomers and/or diastereomers and/or physiologically acceptable salts and/or hydrates and/or solvates thereof calculated as a free base.

The physiologically acceptable compounds formula (I) of the present invention and/or geometric isomers and/or stereoisomers and/or diastereomers and/or physiologically acceptable salts and/or hydrates and/or solvates thereof can normally be administered in a daily dosage regimen (for an adult patient) of, for example, an oral dose between 1 mg and 500 mg, preferably between 10 mg and 400 mg, e.g. between 10 mg and 250 mg or an intravenous, subcutaneous, or intramuscular dose of between 0.1 mg and 100 mg, preferably between 0.1 mg and 50 mg, e.g. between 1 and 25 mg of the compound of formula (I) and/or geometric isomers and/or stereoisomers and/or diastereomers and/or physiologically acceptable salts and/or hydrates and/or solvates thereof calculated as the free base. The compounds of the present invention can be administered 1 to 4 times per day. The compounds of the present invention can suitably be administered for a period of continuous therapy, for example for a week or more.

Biological Test Methods

1. $D_3$ Receptor Binding

Binding study was carried out on rat recombinant $D_3$ receptors (Perkin-Elmer, Cat. No. 6110139) expressed in Sf9 cells using [$^3$H]spiperone (0.44-1.49 nM) as ligand and haloperidol (10 µM) for determination of non-specific binding. The assay was performed according to supplier's assay protocol (Cat. No.: 3110139).

2. $D_2$ Receptor Binding $D_2$ receptor binding was determined as described by Creese et al. (*Eur. J. of Pharm.*, 60:55-66, 1979) on rat brain striatal membrane preparation using [$^3$H]spiperone (0.4-1.3 nM) as ligand. Non-specific binding was determined in the presence of 1 µM (+) butaclamol.

3. α-1 Receptor Binding $α_1$ receptor binding study was performed according to the methods described by Greengrass and Bremner (*Eur. J. Pharmacol.*, 55:323-326, 1979) on rat cortical membrane preparation using [$^3$H]-prazosine (0.22-0.37 nM) as ligand. The non-specific binding was determined in the presence of 10 µM phentolamine.

4. $5\text{-}HT_{1A}$ Binding $5\text{-}HT_{1A}$ receptor binding was determined as described by Hall et al. (*J. Neurochem.* 44:1685-1696, 1985) and Gozlan et al. (*Nature* 305:140-142, 1983) on rat hippocampal membrane preparation using [$^3$H]8-hydroxy-2-(di-n-propylamino)-tetralin (1.6-2.37 nM) as ligand. The non-specific binding was determined in the presence of 10 µM serotonin creatinine sulphate.

Dopamine $D_2$, serotonin $5\text{-}HT_{1A}$ and adrenergic alpha-1 receptor binding data of selected compounds of the present invention are listed in Table 1. $IC_{50}$ (nM) data are given.

TABLE 1

| Compound | $D_3$ | $D_2$ | $5\text{-}HT_{1A}$ | α-1 |
|---|---|---|---|---|
| 1 | <2 | 10 to 40 | 1 to 20 | 40 to 200 |
| 2 | <2 | 10 to 40 | 1 to 20 | 40 to 200 |
| 3 | <2 | 10 to 40 | 1 to 20 | 40 to 200 |
| 4 | <2 | 10 to 40 | 1 to 20 | 40 to 200 |
| 5 | <2 | 10 to 40 | 1 to 20 | 40 to 200 |
| 6 | <2 | 10 to 40 | 1 to 20 | 40 to 200 |
| 9 | <2 | 10 to 40 | 1 to 20 | >200 |
| 10 | <2 | 10 to 40 | 1 to 20 | >200 |
| 11 | <2 | 10 to 40 | 1 to 20 | 40 to 200 |
| 12 | <2 | 10 to 40 | 1 to 20 | 40 to 200 |
| Aripiprazole | 7 | 12 | 26 | 285 |
| Olanzapine | 153 | 147 | 3575 | 46 |

The most prominent side effects of the first generation antipsychotic compounds (e.g. chlorpromazine and haloperidol) are the extrapyramidal symptoms such as pseudo-parkinsonism and tardive dyskinesia and the orthostatic hypotension. The former two are the result of massive blockade of $D_2$ receptors in the basal ganglia whereas the latter is the consequence of antagonism of alpha-1 receptors.

Compounds in Table 1 are very highly potent ligands at $D_3$ receptors ($IC_{50}$ values are less than 2 nM) highly potent ligands at serotonin $5\text{-}HT_{1A}$ receptors ($IC_{50}$ values are between 1 and 20 nM) and moderately potent ligands at dopamine $D_2$ receptors ($IC_{50}$ values are between 10 and 40 nM) showing 5 to 150 fold and 3 to 20 fold selectivity over $D_2$ and $5\text{-}HT_{1A}$ receptors, respectively (selectivity: $IC_{50}$ for $D_2$ or $5\text{-}HT_{1A}$ divided by $IC_{50}$ for $D_3$). Such association of the very high D$_3$ affinity to the high 5-HT$_{1A}$ and moderate D$_2$ affinity in this particular proportion allows to preserve the beneficial (e.g. antipsychotic) actions of a D$_2$ antagonist while—at the same time—impedes (by the D$_3$ and 5-HT$_{1A}$ effects) the appearance of the disadvantageous consequences of massive D$_2$ receptor blockade like extrapyramidal symptoms or cognitive disturbances. It is therefore anticipated that no or greatly diminished adverse effects related to D$_2$ receptors will occur in the course of therapeutical application of compounds of the present invention. Furthermore, beside favourably modulating the dopamine D$_2$ receptor-mediated functions action of the compounds of the present invention on dopamine D$_3$ and serotonin 5-HT$_{1A}$ receptors will also result in additional therapeutically beneficial effects e.g. cognitive improvement, diminution of negative and depressive symptoms or anxiolysis. In addition, the compounds have slight or low affinity to adrenergic alpha-1 receptors (IC-50 higher than 40 nM for each compound) and thus have extremely high D$_3$/alpha-1 selectivity (ranging from hundred-fold to several hundred-fold). From the low affinity of the compounds to adrenergic alpha-1 receptors the lack of cardiovascular side effects (e.g. orthostatic hypotension) is anticipated.

With respect to the expected clinical application of the compounds of the present invention in addition to their receptor binding profile their in vivo efficacy is a crucial issue as well. Therefore, in vivo potency and efficacy of the compounds of formula (I) were studied in the apomorphine climbing assay, an animal screening test for antipsychotic activity.

5. Inhibition of Apomorphine Induced Climbing

Male CD-1 mice weighing 20-25 g were injected orally (n=12) with the test compound or vehicle. Fifty minutes later the animals were placed into cylindrical cages with walls of vertical metal bars. After 10 minutes habituation the mice were treated with apomorphine (1.5 mg/kg sc.). Ten minutes after APO treatment each animal was observed for 15 minutes and scored for their climbing behaviour. Scores were summed for each individual and group means were calculated. Drug effect was expressed and plotted as percentage inhibition of the apomorphine induced behaviour. ED$_{50}$ (50% inhibitory dose) values were determined by linear regression.

In vivo activity of selected compounds of the present invention is shown in Table 2. ED$_{50}$ (mg/kg) data obtained in the apomorphine climbing assay are given.

TABLE 2

| Compound | Inhibition of climbing |
| --- | --- |
| 1 | 0.14 |
| 2 | 0.21 |
| 3 | 0.11 |
| 4 | 0.46 |
| 5 | 0.47 |
| 6 | 0.16 |
| 9 | 0.26 |
| 10 | 0.35 |
| 11 | 0.23 |
| 12 | 0.20 |
| Aripiprazole | 1.0 |
| Olanzapine | 1.3 |

All the compounds tested showed exceptionally potent inhibition against apomorphine in mice being 2 to 12 times more potent than the reference drugs olanzapine or aripiprazole. The most active compounds proved to be compound 1, 3 and 6.

The invention is further illustrated by the following non-limiting examples.

The structure of all intermediates and end products were elucidated by IR, NMR and MS spectroscopy.

EXAMPLE 1

Trans-4-{2-[4-(indan-4-yl)-piperazin-1-yl]-ethyl}-cyclohexyl-carbamic acid tert-butylester (intermediate)

3.58 g (15 mmol) of 1-(indan-4-yl)-piperazine hydrochloride and 3.62 g (15 mmol) of trans-4-(2-oxoethyl)cyclohexyl-carbamic acid tert-butyl ester were dissolved in dichloroethane (120 ml), 2.1 ml (15 mmol) triethylamine was added, then 4.6 g (22 mmol) sodium triacetoxyborohydride was added portionswise and the reaction mixture was stirred for 20 hours at ambient temperature, then 20% potassium carbonate solution in water (40 ml) was added. The organic layer was separated, dried and evaporated to dryness in vacuo. The precipitate was recrystallized from acetonitrile to give the title compound 5.5 g (yield: 85.8%), m.p.: 115-8° C.

EXAMPLE 2

Trans-4-{4-(indan-4-yl)-piperazin-1-yl-methyl}-cyclohexyl-carbamic acid tert-butylester (intermediate)

3.58 g (15 mmol) of 1-(indan-4-yl)-piperazine hydrochloride and 3.41 g (15 mmol) of trans-(4-formyl-cyclohexyl)-carbamic acid tert-butylester were dissolved in dichloroethane (120 ml), 2.1 ml (15 mmol) triethylamine was added, then 4.6 g (22 mmol) sodium triacetoxyborohydride was added portionswise and the reaction mixture was stirred for 20 hours at ambient temperature, then 20% potassium carbonate solution in water (40 ml) was added. The organic layer was separated, dried and evaporated to dryness in vacuo. The precipitate was recrystallized from acetonitrile to give the title compound 5.1 g (yield: 82.2%), m.p.: 131-4° C.

EXAMPLE 3

Trans-4-{2-[4-(indan-4-yl)-piperazin-1-yl]-ethyl}-cyclohexyl-amine (intermediate)

4.24 g (10 mmol) trans-4-{2-[4-(indan-4-yl)-piperazin-1-yl]-ethyl}-cyclohexyl-carbamic acid tert-butylester was deprotected at 10° C. using 80 ml ethylacetate saturated with gaseous hydrochloric acid, after 4 hours the precipitate was filtered giving 3.65 g (yield: 92%) dihydrochloride salt of the title compound, melting at 319-25° C.

Applying the above procedure the following compound was prepared:
trans-4-[4-(indan-4-yl)-piperazin-1-yl-methyl]-cyclohexyl-amine trihydrochloride, melting point: 305-10° C.
Method A Trans-1-{4-[2-[4-(indan-4-yl)-piperazin-1-yl]-ethyl]-cyclohexyl}-3,3-dimethyl-urea 0.4 g (1 mmol) trans-4-{2-[4-(indan-4-yl)-piperazin-1-yl]-ethyl}-cyclohexyl-amine dihydrochloride was suspended in dichloromethane (30 ml), triethylamine (0.56 ml, 4 mmol) was added followed by 0.12 ml (1.3 mmol) N,N-dimethyl-carbamoylchloride. The reaction mixture was stirred for 24 hours at room temperature. The solution was extracted with water (2×8 ml), dried and evaporated in vacuo. The residue was purified using flash chromatography giving the title compound (0.2 g, 50%), melting at 150-2° C.
Method B Trans-1-{4-[2-[4-(indan-4-yl)-piperazin-1-yl]-ethyl]-cyclohexyl}-3-ethyl-urea 0.4 g (1 mmol) trans-4-{2-[4-(indan-4-yl)-piperazin-1-yl]-ethyl}-cyclohexyl-amine was dissolved in dry dichloromethane (30 ml), ethylisocyanate (0.1 ml, 1.3 mmol) was added and the reaction mixture was stirred at room temperature for 4 hours. The solvent was removed in vacuo. The residue was recrystallized from acetonitrile giving the title compound (0.22 g, 55%), melting at 198-200° C.
Method C Trans-1-{4-[2-[4-(indan-4-yl)-piperazin-1-yl]-ethyl]-cyclohexyl}-3,3-diethyl-urea 0.48 g (1.2 mmol) trans-4-{2-[4-(indan-4-yl)-piperazin-1-yl]-ethyl}-cyclohexyl-amine dihydrochloride was suspended in dry dichloromethane (50 ml), triethylamine 0.67 ml, 4.8 mmol) was added and 0.14 g (0.48 mmol) triphosgene dissolved in dichloromethane was dropped in. After one hour stirring at room temperature diethylamine (0.62 ml, 6 mmol) was added and the stirring was continued for 20 hours. The solution was extracted with water (2×8 ml), dried and evaporated in vacuo. The residue was purified using flash chromatography giving the title compound (0.3 g, 58%), melting point: 157-9° C.

Applying one of the above methods using the appropriate reactants the following compounds were prepared:

trans-N-{4-[2-[4-(indan-4-yl)-piperazin-1-yl]-ethyl]-cyclohexyl}-acetamide (compound 1) melting point: 202-4° C.;

trans-N-{4-[2-[4-(indan-4-yl)-piperazin-1-yl]-ethyl]-cyclohexyl}-propionamide (compound 2) melting point: 194-6° C.;

trans-1-{4-[2-[4-(indan-4-yl)-piperazin-1-yl]-ethyl]-cyclohexyl}-3,3-dimethyl-urea (compound 3) melting point: 150-2° C.;

trans-1-{4-[2-[4-(indan-4-yl)-piperazin-1-yl]-ethyl]-cyclohexyl}-3,3-diethyl-urea (compound 4) melting point: 157-9° C.;

trans-1-{4-[2-[4-(indan-4-yl)-piperazin-1-yl]-ethyl]-cyclohexyl}-3-ethyl-urea (compound 5) melting point: 198-200° C.;

trans-N-{4-[2-[4-(indan-4-yl)-piperazin-1-yl]-ethyl]-cyclohexyl}-morpholine-4-carboxamide (compound 6) melting point: 181-2° C.;

trans-1-{4-[2-[4-(indan-4-yl)-piperazin-1-yl]-ethyl]-cyclohexyl}-urea (compound 7) melting point: 204-6° C.;

trans-1-{4-[[4-(indan-4-yl)-piperazin-1-yl]-methyl]-cyclohexyl}-3,3-dimethyl-urea (compound 8) melting point: 152-154° C.;

trans-N-{4-[2-[4-(5,6,7,8-tetrahydronaphthalen-1-yl)-piperazin-1-yl]-ethyl]-cyclohexyl}-acetamide (compound 9) melting point: 187-9° C.;

trans-N-{4-[2-[4-(5,6,7,8-tetrahydronaphthalen-1-yl)-piperazin-1-yl]-ethyl]-cyclohexyl}-propionamide (compound 10) melting point: 182-5° C.;

trans-1-{4-[2-[4-(5,6,7,8-tetrahydronaphthalen-1-yl)-piperazin-1-yl]-ethyl]-cyclohexyl}-3,3-dimethyl-urea (compound 11) melting point: 190-3° C.;

trans-N-{4-[2-[4-(5,6,7,8-tetrahydronaphthalen-1-yl)-piperazin-1-yl]-ethyl]-cyclohexyl}-morpholine-4-carboxamide (compound 12) melting point: 178-80° C.

Pharmaceutical Formulations a) Intravenous Injection

| Compound of formula (I) | 1-40 mg |
|---|---|
| Buffer | to pH ca 7 |
| Solvent/complexing agent | to 100 ml | b) Bolus Injection

| Compound of formula (I) | 1-40 mg |
|---|---|
| Buffer | to pH ca 7 |
| Co-solvent | to 5 ml |

Buffer: suitable buffers include citrate, phosphate, sodium hydroxide/hydrochloric acid.

Solvent: typically water but may also include cyclodextrins (1-100 mg) and co-solvents, such as propylene glycol, polyethylene glycol and alcohol.

c) Tablet

| Compound of formula (I) | 1-40 mg |
|---|---|
| Diluent/Filter(may also include cyclodextrins) | 50-250 mg |
| Binder | 5-25 mg |
| Disintegrant (may also include cyclodextrins) | 5-50 mg |
| Lubricant | 1-5 mg |
| Cyclodextrin | 1-100 mg |

Diluent: e.g. microcrystalline cellulose, lactose starch.

Binder: e.g. polyvinylpyrrolidone, hydroxypropylmethylcellulose.

Disintegrant: e.g. sodium starch glycolate, crospovidone.

Lubricant: e.g. magnesium stearate, sodium stearyl fumarate d) Oral Suspension

| Compound of formula (I) | 1-40 mg |
|---|---|
| Suspending agent | 0.1-10 mg |
| Diluent | 20-60 mg |
| Preservative | 0.01-1.0 mg |
| Buffer | to pH ca 5-8 |
| Co-solvent | 0-40 mg |
| Flavour | 0.01-1.0 mg |
| Colourant | 0.001-0.1 mg |

Suspending agent: e.g. xanthan gum, microcrystalline cellulose.

Diluent: e.g. sorbitol solution, typically water.

Preservative: e.g. sodium benzoate.

Buffer: e.g. citrate.

Co-solvent: e.g. alcohol, propylene glycol, polyethylene glycol, cyclodextrin.

What we claim:

1. A compound of formula (I):

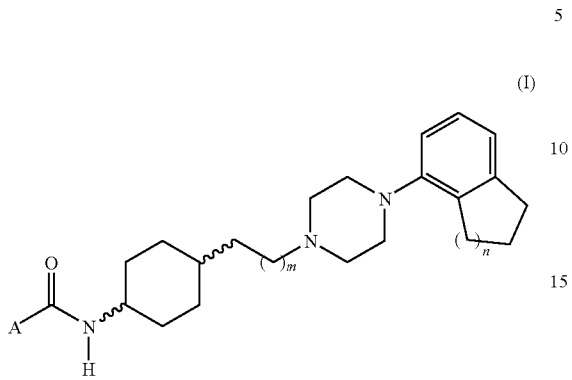

wherein
A represents alkyl, alkenyl, aryl, heteroaryl, cycloalkyl or a group of formula —$NR_1R_2$, wherein
$R_1$ and $R_2$ represent independently a substituent selected from hydrogen, alkyl, alkenyl, aryl, heteroaryl or cycloalkyl or $R_1$ and $R_2$ form with the adjacent nitrogen atom and optionally with further heteroatom(s) a heterocyclic ring;
m is an integer of 0 to 1; and
n is an integer of 1 to 2,
and/or geometric isomers and/or stereoisomers and/or diastereomers and/or salts thereof.

2. A compound of formula (I) as claimed in claim 1:

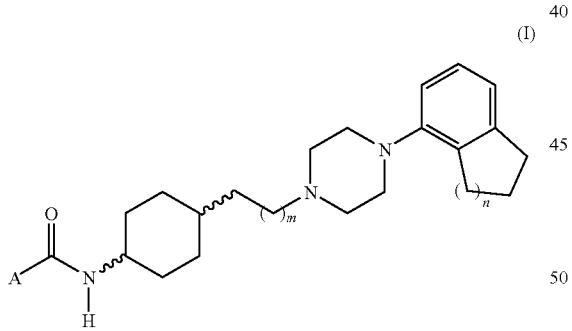

wherein
A represents alkyl, or
a group of formula —$NR_1R_2$, wherein
$R_1$ and $R_2$ represent independently a substituent selected from hydrogen or alkyl, or $R_1$ and $R_2$ form with the adjacent nitrogen atom and optionally with further heteroatom(s) selected from O, N, or S a monocyclic saturated heterocyclic ring;
m is an integer of 0 to 1; and
n is an integer of 1 to 2,
and/or geometric isomers and/or stereoisomers and/or diastereomers and/or salts thereof.

3. A compound of formula (I) as claimed in claim 1:

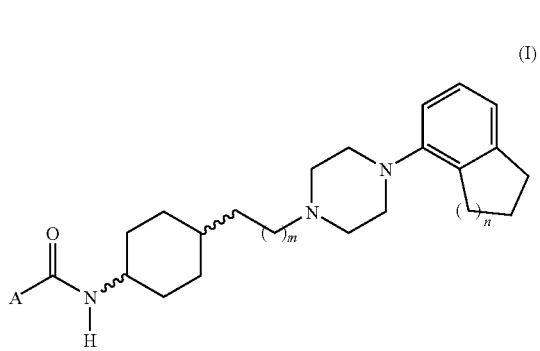

wherein
A represents $C_{1-4}$ alkyl, or
a group of formula —$NR_1R_2$, wherein
$R_1$ and $R_2$ represent independently a substituent selected from hydrogen or
$C_{1-4}$ alkyl, or $R_1$ and $R_2$ form with the adjacent nitrogen atom and with an oxygen atom a morpholine ring;
m is an integer of 0 to 1; and
n is an integer of 1 to 2,
and/or geometric isomers and/or stereoisomers and/or diastereomers and/or salts thereof.

4. A compound selected from:
trans-N-{4-[2-[4-(indan-4-yl)-piperazin-1-yl]-ethyl]-cyclohexyl}-acetamide,
trans-N-{4-[2-[4-(indan-4-yl)-piperazin-1-yl]-ethyl]-cyclohexyl}-propionamide,
trans-1-{4-[2-[4-(indan-4-yl)-piperazin-1-yl]-ethyl]-cyclohexyl}-3,3-dimethyl-urea,
trans-1-{4-[2-[4-(indan-4-yl)-piperazin-1-yl]-ethyl]-cyclohexyl}-3,3-diethyl-urea,
trans-1-{4-[2-[4-(indan-4-yl)-piperazin-1-yl]-ethyl]-cyclohexyl}-3-ethyl-urea,
trans-N-{4-[2-[4-(indan-4-yl)-piperazin-1-yl]-ethyl]-cyclohexyl}-morpholine-4-carboxamide,
trans-1-{4-[2-[4-(indan-4-yl)-piperazin-1-yl]-ethyl]-cyclohexyl}-urea,
trans-1-{4-[4-(indan-4-yl)-piperazin-1-yl]-methyl}-cyclohexyl}-3,3-dimethyl-urea,
trans-N-{4-[2-[4-(5,6,7,8-tetrahydronaphthalen-1-yl)-piperazin-1-yl]-ethyl]-cyclohexyl}-acetamide,
trans-N-{4-[2-[4-(5,6,7,8-tetrahydronaphthalen-1-yl)-piperazin-1-yl]-ethyl]-cyclohexyl}-propionamide,
trans-1-{4-[2-[4-(5,6,7,8-tetrahydronaphthalen-1-yl)-piperazin-1-yl]-ethyl]-cyclohexyl}-3,3-dimethyl-urea, and
trans-N-{4-[2-[4-(5,6,7,8-tetrahydronaphthalen-1-yl)-piperazin-1-yl]-ethyl]-cyclohexyl}-morpholine-4-carboxamide.

5. An amine of formula (III):

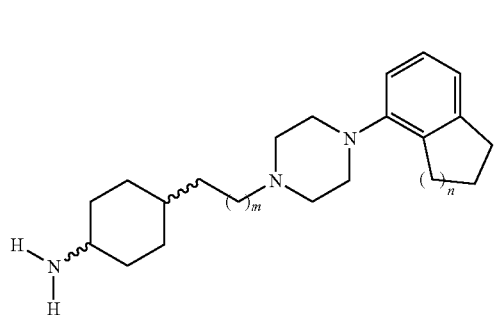

wherein
  m is an integer of 0 to 1; and
  n is an integer of 1 to 2,
and/or protected forms thereof and/or geometric isomers and/or salts thereof.

6. An isocyanate of formula (V):

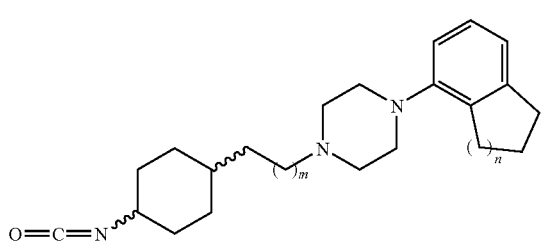

wherein
  m is an integer of 0 to 1; and
  n is an integer of 1 to 2,
and/or geometric isomers and/or salts thereof.

7. A process
  a) for preparing a compound of formula (I):

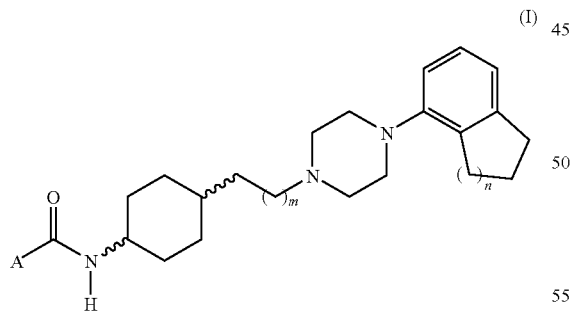

wherein
  A represents alkyl, alkenyl, aryl, heteroaryl, cycloalkyl or a group of formula —$NR_1R_2$, wherein
    $R_1$ and $R_2$ represent independently a substituent selected from hydrogen, alkyl, alkenyl, aryl, heteroaryl or cycloalkyl or $R_1$ and $R_2$ form with the adjacent nitrogen atom and optionally with further heteroatom(s) a heterocyclic ring;
  m is an integer of 0 to 1; and
  n is an integer of 1 to 2, and/or geometric isomers and/or stereoisomers and/or diastereomers and/or salts and/or hydrates and/or solvates thereof, which comprises:
  reacting an acid- or carbamoylchloride of formula (II):

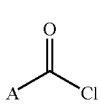

wherein the meaning of A is as described above for the formula (I);
  with an amine of formula (III):

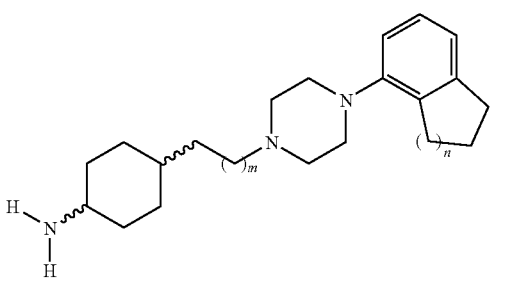

wherein the meaning of m and n is as described above for the formula (I),
  or derivatives thereof, or
  b) for preparing a compound of formula (I):

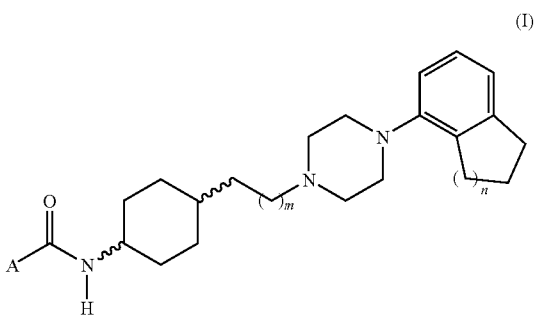

wherein
  A represents a group of formula —$NR_1R_2$, wherein
    $R_2$ represents hydrogen, and $R_1$ represents a substituent selected from hydrogen, alkyl, alkenyl, aryl, heteroaryl or cycloalkyl;
  m is an integer of 0 to 1; and
  n is an integer of 1 to 2,
and/or geometric isomers and/or stereoisomers and/or diastereomers and/or salts thereof, which comprises:
  reacting an isocyanate of formula (IV):

wherein the meaning of $R_1$ is as described above for the formula (I), with an amine of formula (III):

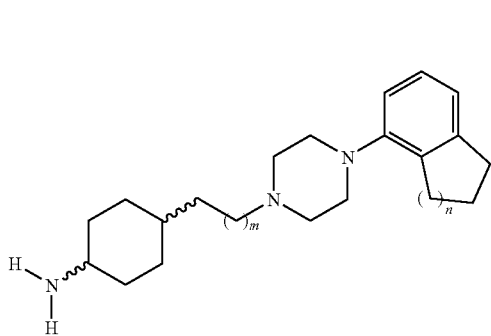

wherein the meaning of m and n is as described above for the formula (I),
or derivatives thereof, or
c) for preparing a compound of formula (I):

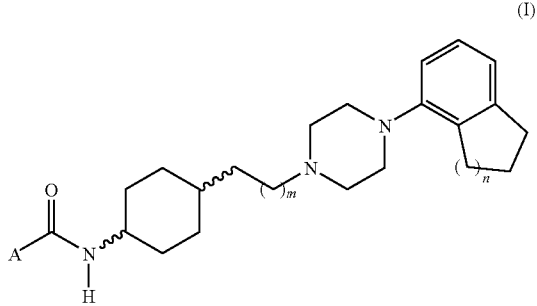

wherein
A represents a group of formula —$NR_1R_2$, wherein
$R_1$ and $R_2$ represent independently a substituent selected from hydrogen, alkyl, alkenyl, aryl, heteroaryl or cycloalkyl or $R_1$ and $R_2$ form with the adjacent nitrogen atom and optionally with further heteroatom(s) a heterocyclic ring;
m is an integer of 0 to 1; and
n is an integer of 1 to 2,
and/or geometric isomers and/or stereoisomers and/or diastereomers and/or salts thereof, which comprises:
reacting an amine of formula (III):

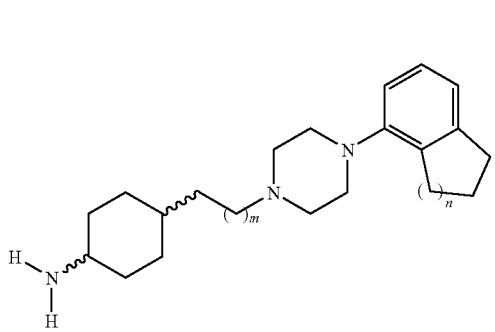

wherein the meaning of m and n is as described above for the formula (I),
or derivatives thereof,
with a carbonic acid derivative to obtain an isocyanate derivative of formula (V):

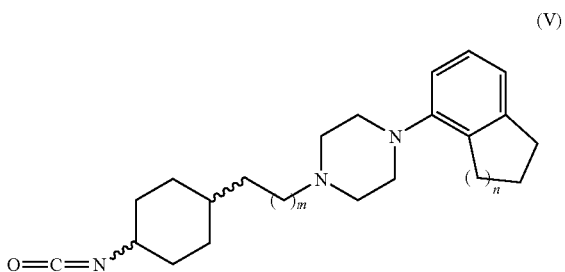

wherein the meaning of m and n is as described above for the formula (I),
and reacting in situ the isocyanate derivative of formula (V) with an amine of formula (VI):

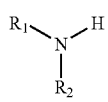

wherein the meaning of $R_1$ and $R_2$ are as described above for the formula (I),
or derivatives thereof, and
interconverting one compound of formula (I) obtained by any of method a) to c), wherein A, m and n are as defined for compound of formula (I) to a different compound of formula (I) wherein A, m and n are as defined for compound of formula (I);
where appropriate, separating the geometric isomers and/or stereoisomers and/or diastereomers of compounds of formula (I), or intermediates thereof, wherein A, m and n are as defined for compound of formula (I);
and optionally thereafter forming salts of compound of formula (I).

8. A process according to claim 7
a) for preparing a compound of the general formula (I):

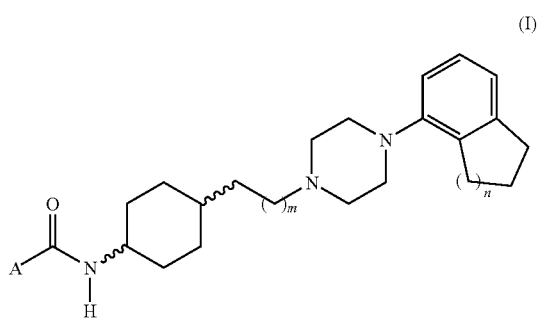

wherein
A represents alkyl, or
a group of formula —$NR_1R_2$, wherein
$R_1$ and $R_2$ represent independently a substituent selected from hydrogen or alkyl, or $R_1$ and $R_2$ form with the adjacent nitrogen atom and optionally with further heteroatom(s) selected from O, N, or S a monocyclic saturated heterocyclic ring;
m is an integer of 0 to 1; and
n is an integer of 1 to 2, and/or geometric isomers and/or stereoisomers and/or diastereomers and/or salts and/or hydrates and/or solvates thereof, which comprises:

reacting an acid- or carbamoylchloride of formula (II):

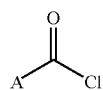
(II)

wherein the meaning of A is as described above for the formula (I);

with an amine of formula (III):

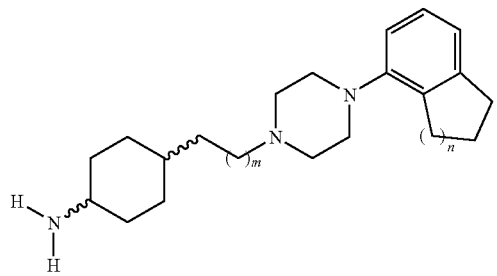
(III)

wherein the meaning of m and n is as described above for the formula (I),
or derivatives thereof, or b) for preparing a compound of formula (I):

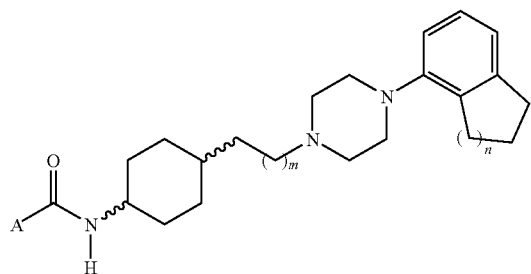
(I)

wherein

A represents a group of formula —NR₁R₂, wherein
R₂ represents hydrogen, and R₁ represents hydrogen or alkyl;
m is an integer of 0 to 1; and
n is an integer of 1 to 2, and/or geometric isomers and/or stereoisomers and/or diastereomers and/or salts thereof, which comprises:

reacting an isocyanate of formula (IV):

R₁—N=C=O  (IV)

wherein the meaning of R₁ is as described above for the formula (I), with an amine of formula (III):

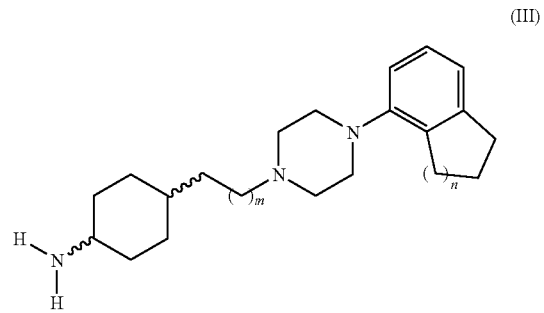
(III)

wherein the meaning of m and n is as described above for the formula (I),
or derivatives thereof, or c) for preparing a compound of formula (I):

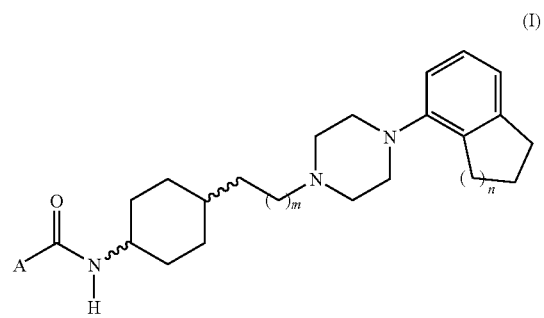
(I)

wherein

A represents a group of formula —NR₁R₂,
wherein R₁ and R₂ represent independently a substituent selected from hydrogen or alkyl, or R₁ and R₂ form with the adjacent nitrogen atom and optionally with further heteroatom(s) selected from O, N, or S a monocyclic saturated heterocyclic ring;
m is an integer of 0 to 1; and
n is an integer of 1 to 2, and/or geometric isomers and/or stereoisomers and/or diastereomers and/or salts thereof, which comprises:

reacting an amine of formula (III):

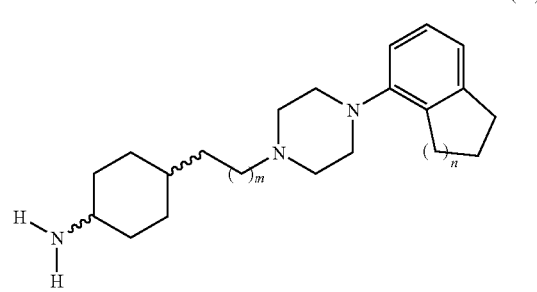
(III)

wherein the meaning of m and n is as described above for the formula (I),
or derivatives thereof,
with a carbonic acid derivative to obtain an isocyanate derivative of formula (V):

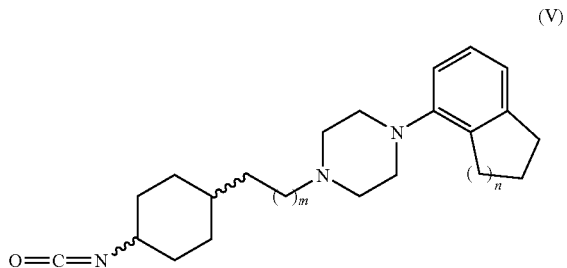
(V)

wherein the meaning of m and n is as described above for the formula (I),
and reacting in situ the isocyanate derivative of formula (V) with an amine of formula (VI):

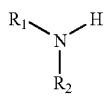
(VI)

wherein the meaning of $R_1$ and $R_2$ are as described above for the formula (I),
or derivatives thereof, and
interconverting one compound of formula (I) obtained by any of method a) to c), wherein A, m and n are as defined for compound of formula (I) to a different compound of formula (I) wherein A, m and n are as defined for compound of formula (I);
where appropriate, separating the geometric isomers and/or stereoisomers and/or diastereomers of compounds of formula (I), or intermediates thereof, wherein A, m and n are as defined for compound of formula (I);
and optionally thereafter forming salts of compound of formula (I).

9. A process according to claim 7
a) for preparing a compound of formula (I):

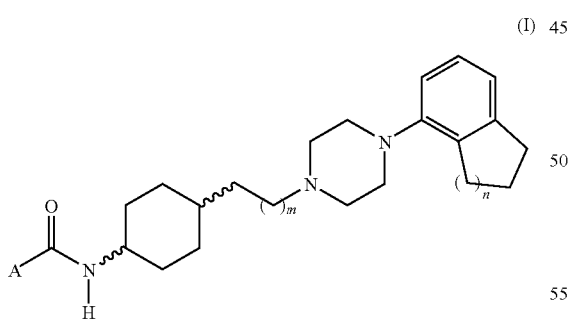
(I)

wherein
A represents $C_{1-4}$ alkyl, or
a group of formula —$NR_1R_2$, wherein
$R_1$ and $R_2$ represent independently a substituent selected from hydrogen or $C_{1-4}$ alkyl, or $R_1$ and $R_2$ form with the adjacent nitrogen atom and with an oxygen atom a morpholine ring;
m is an integer of 0 to 1; and
n is an integer of 1 to 2, and/or geometric isomers and/or stereoisomers and/or diastereomers and/or salts and/or hydrates and/or solvates thereof, which comprises:
reacting an acid- or carbamoylchloride of formula (II):

(II)

wherein the meaning of A is as described above for the formula (I);
with an amine of formula (III):

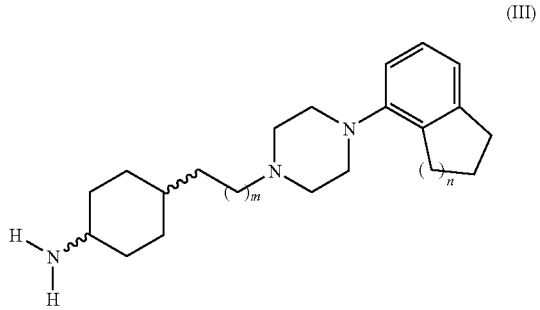
(III)

wherein the meaning of m and n is as described above for the formula (I),
or derivatives thereof, or
b) for preparing a compound of formula (I),

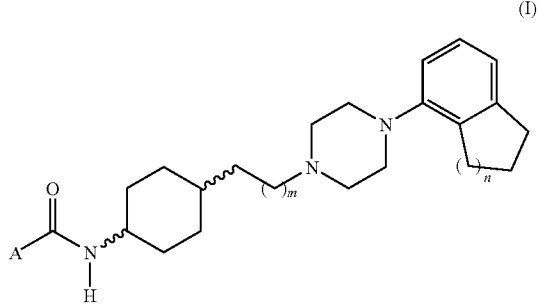
(I)

wherein
A represents a group of formula —$NR_1R_2$, wherein
$R_2$ represents hydrogen and $R_1$ represents hydrogen or $C_{1-4}$ alkyl;
m is an integer of 0 to 1; and
n is an integer of 1 to 2,
and/or geometric isomers and/or stereoisomers and/or diastereomers and/or salts thereof, which comprises:
reacting an isocyanate of formula (IV):

(IV)

wherein the meaning of $R_1$ is as described above for the formula (I), with an amine of formula (III):

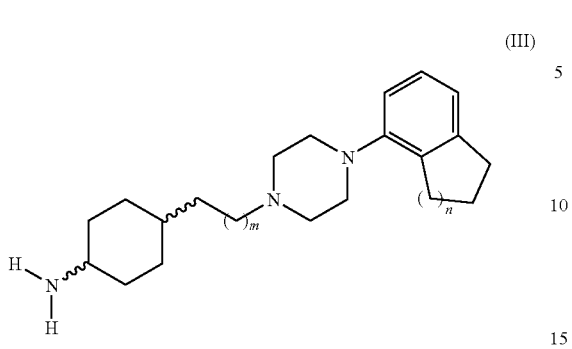

wherein the meaning of m and n is as described above for the formula (I),
or derivatives thereof, or
c) for preparing a compound of formula (I):

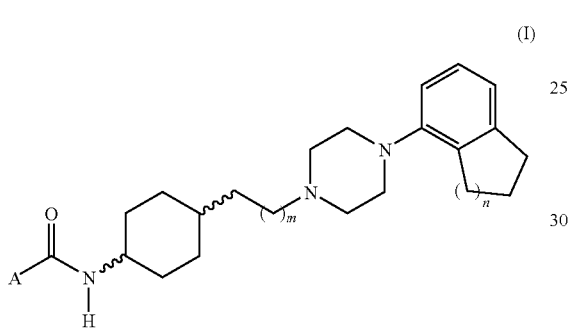

wherein
A represents a group of formula —$NR_1R_2$, wherein
$R_1$ and $R_2$ represent independently a substituent selected from hydrogen or $C_{1-4}$ alkyl, or $R_1$ and $R_2$ form with the adjacent nitrogen atom and with an oxygen atom a morpholine ring;
m is an integer of 0 to 1; and
n is an integer of 1 to 2,
and/or geometric isomers and/or stereoisomers and/or diastereomers and/or salts thereof, which comprises:
reacting an amine of formula (III):

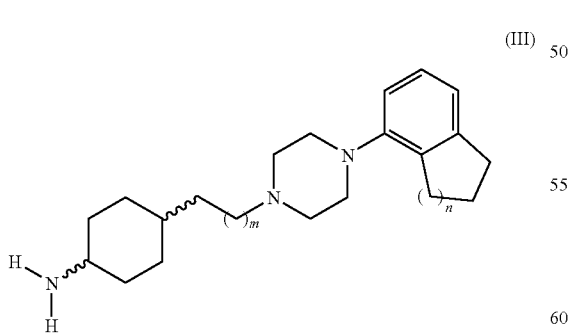

wherein the meaning of m and n is as described above for the formula (I),
or derivatives thereof
with a carbonic acid derivative to an isocyanate derivative of formula (V):

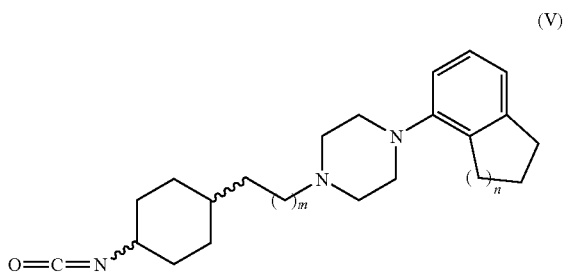

wherein the meaning of m and n is as described above for the formula (I),
and reacting in situ the isocyanate derivative of formula (V) with an amine of formula (VI):

wherein $R_1$ and $R_2$ are as described above for the formula (I), or derivatives thereof, and
interconverting one compound of formula (I) obtained by any of method a) to c), wherein A, m and n are as defined for compound of formula (I) to a different compound of formula (I) wherein A, m and n are as defined for compound of formula (I);
where appropriate, separating the geometric isomers and or stereoisomers and/or diastereomers of compounds of formula (I), or intermediates thereof, wherein A, m and n are as defined for compound of formula (I);
and optionally thereafter forming salts of compound of formula (I).

10. A pharmaceutical composition comprising a compound of formula (I):

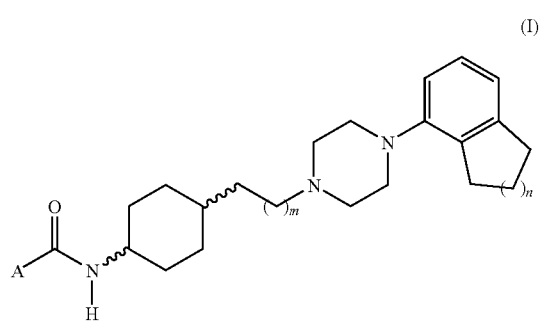

wherein
A represents alkyl, alkenyl, aryl, heteroaryl, cycloalkyl or a group of formula —$NR_1R_2$, wherein
$R_1$ and $R_2$ represent independently a substituent selected from hydrogen, alkyl, alkenyl, aryl, heteroaryl or cycloalkyl or $R_1$ and $R_2$ form with the adjacent nitrogen atom and optionally with further heteroatom(s) a heterocyclic ring;
m is an integer of 0 to 1; and
n is an integer of 1 to 2, and/or geometric isomers and/or stereoisomers and/or diastereomers and/or physiologically acceptable salts thereof and physiologically acceptable carrier(s) therefore.

11. A pharmaceutical composition comprising a compound of formula (I):

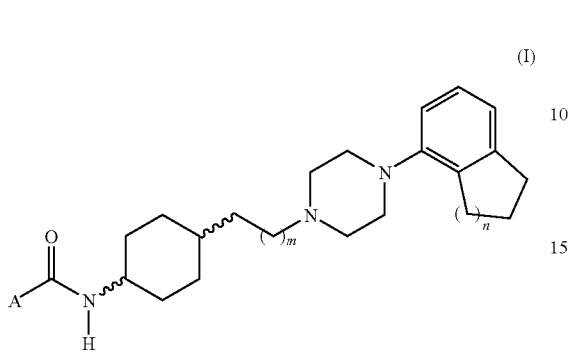

as claimed in claim 10,
wherein
A represents alkyl, or
a group of formula —NR$_1$R$_2$, wherein
R$_1$ and R$_2$ represent independently a substituent selected from hydrogen or alkyl, or R$_1$ and R$_2$ form with the adjacent nitrogen atom and optionally with further heteroatom(s) selected from O, N, or S a monocyclic saturated heterocyclic ring;
m is an integer of 0 to 1; and
n is an integer of 1 to 2,
and/or geometric isomers and/or stereoisomers and/or diastereomers and/or physiologically acceptable salts thereof and physiologically acceptable carrier(s) therefore.

12. A pharmaceutical composition comprising a compound of formula (I):

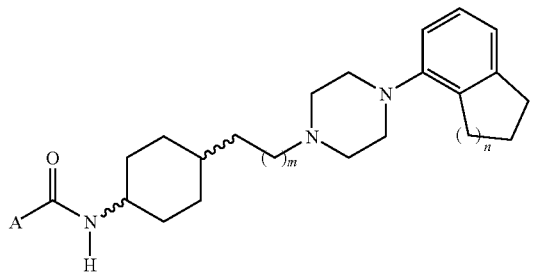

as claimed in claim 10,
wherein
A represents C$_{1-4}$ alkyl, or
a group of formula —NR$_1$R$_2$, wherein
R$_1$ and R$_2$ represent independently a substituent selected from hydrogen or C$_{1-4}$ alkyl, or R$_1$ and R$_2$ form with the adjacent nitrogen atom and with an oxygen atom a morpholine ring;
m is an integer of 0 to 1; and
n is an integer of 1 to 2,
and/or geometric isomers and/or stereoisomers and/or diastereomers and/or physiologically acceptable salts thereof and physiologically acceptable carrier(s) therefore.

* * * * *